United States Patent
Isgor et al.

(10) Patent No.: US 12,194,058 B2
(45) Date of Patent: Jan. 14, 2025

(54) CANCER TREATMENT REGIMEN USING ANTI-PARASITIC COMPOUNDS AND GUT MICROBIOME MODULATING AGENTS

(71) Applicant: FLORIDA ATLANTIC UNIVERSITY BOARD OF TRUSTEES, Boca Raton, FL (US)

(72) Inventors: Ceylan Isgor, Delray Beach, FL (US); Vijaya Iragavarapu, Boca Raton, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 0 days.

(21) Appl. No.: 18/270,344

(22) PCT Filed: Jan. 5, 2022

(86) PCT No.: PCT/US2022/011277
§ 371 (c)(1),
(2) Date: Jun. 29, 2023

(87) PCT Pub. No.: WO2022/150356
PCT Pub. Date: Jul. 14, 2022

(65) Prior Publication Data
US 2024/0082294 A1    Mar. 14, 2024

Related U.S. Application Data

(60) Provisional application No. 63/134,259, filed on Jan. 6, 2021.

(51) Int. Cl.
| | | |
|---|---|---|
| *A61K 31/722* | (2006.01) | |
| *A61K 31/4184* | (2006.01) | |
| *A61K 45/06* | (2006.01) | |
| *A61P 35/00* | (2006.01) | |

(52) U.S. Cl.
CPC ........ *A61K 31/722* (2013.01); *A61K 31/4184* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 10,766,970 B2 | 9/2020 | Welker et al. | |
| 2003/0054042 A1* | 3/2003 | Liversidge | A61P 37/06 424/489 |
| 2009/0061010 A1 | 3/2009 | Zale et al. | |
| 2012/0058194 A1* | 3/2012 | Vaya | A61K 9/5026 424/494 |
| 2016/0143961 A1 | 5/2016 | Berry et al. | |
| 2022/0323357 A1* | 10/2022 | Fernandes | A61K 9/143 |
| 2022/0339294 A1* | 10/2022 | Mandl | A61P 7/00 |

FOREIGN PATENT DOCUMENTS

WO    WO-9632107 A1 * 10/1996 ........... A61K 31/415

OTHER PUBLICATIONS

Satish Kumar et al. "Chitosan-Gold Nanoparticles as Delivery Systems for Curcumin" International Journal of Pharmaceutical Sciences and Research Oct. 2012 pp. 4533-4539.
Son et al. "The Antitumor Potentials of Benzimidazole Anthelmintics as Repurposing Drugs" Immune Network Jul. 2020, pp. 1-20.
Albalawi et al. "High Potency of Organic and Inorganic Nanoparticles to Treat Cystic Echinococcosis: An Evidence-Based Review" Nanomaterials Dec. 17, 2020, pp. 1-17.
Lee et al. "Chitosan oligosaccharides, dp 2-8, have prebiotic effect on the Bifidobacterium bifidium and *Lactobacillus* sp." Food Microbiology, Feb. 2003, pp. 319-324.
International Search Report and Written Opinion issued in PCT/US2022/011277, mailed May 13, 2022.

* cited by examiner

*Primary Examiner* — John Pak
(74) *Attorney, Agent, or Firm* — Meunier Carlin & Curfman LLC

(57) ABSTRACT

A composition and method of cancer treatment including a) administering to a patient a first anti-parasitic agent; b) administering to the patient a second anti-parasitic agent; and c) administering to the patient a gut microbiome modulating agent; wherein the first anti-parasitic agent and the second anti-parasitic agent are administered concurrently for a predetermined first period of time; and wherein the gut microbiome modulating agent is administered for a predetermined second period of time.

12 Claims, 9 Drawing Sheets

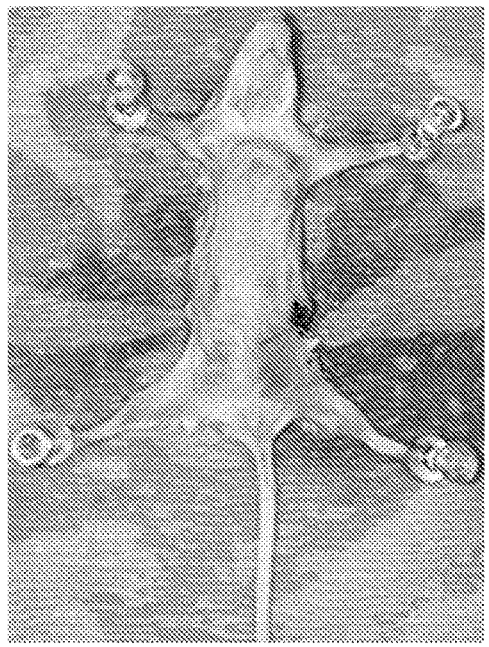 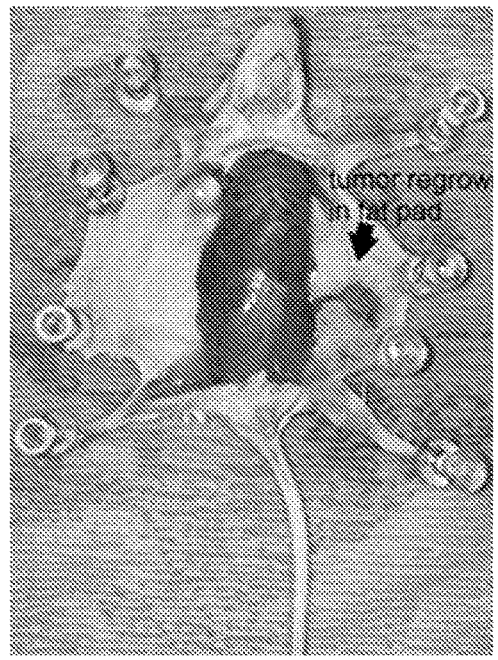
FIG. 10A  FIG. 10B
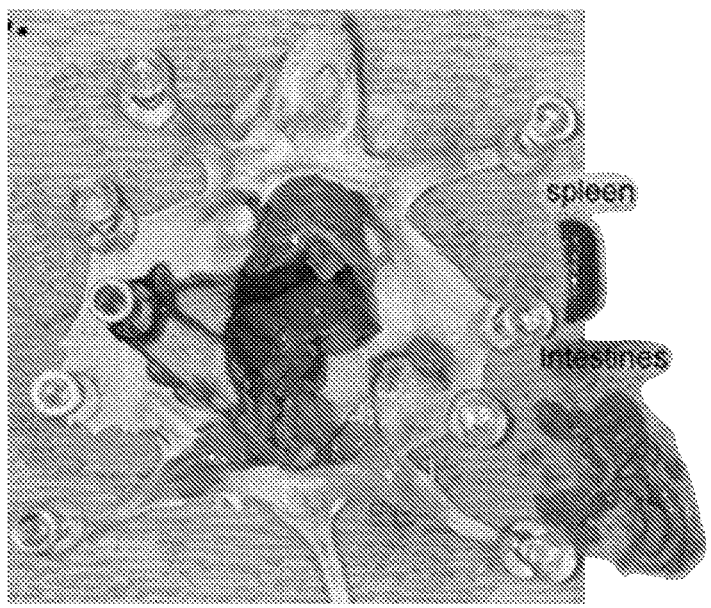 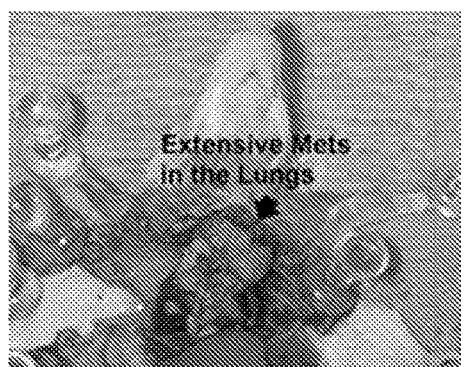
FIG. 10C  FIG. 10D

CANCER TREATMENT REGIMEN USING ANTI-PARASITIC COMPOUNDS AND GUT MICROBIOME MODULATING AGENTS

CROSS-REFERENCE TO RELATED APPLICATIONS

This PCT application claims the benefit of 35 U.S.C. § 119(e) of Application Ser. No. 63/134,259, filed on Jan. 6, 2021, entitled CANCER TREATMENT REGIMEN and whose entire disclosure is incorporated by reference herein.

FIELD OF THE INVENTION

This invention is directed to the field of cancer treatment and, in particular, a treatment and method using one or more anti-parasitic compounds, in combination with gut microbiome modulating oral therapy.

BACKGROUND OF THE INVENTION

Cancer is a multi-factorial pathology and well known to be one of the leading causes of death worldwide. Fenbendazole is an anti-parasitic drug that acts as a microtubule destabilizing agent that may have anti-tumor effects in cell lines (Nilarnbra Dogra, et al. 2018, Scientific Reports). Laboratory testing using cultured tumor cells indicate that benzimidazoles in general, and fenbendazole in particular, cause tumor cell death and arrest tumor cell division (Zuzana Mrkvova, et al., 2019, Molecules). While there are no known studies conducted on humans to explore the possibility of benzimidazole shrinking tumors in patients with end stage cancer, it is known that the body can develop a resistance to benzimidazole. Resistance develops to anthelmintic effects of benzimidazoles after initial success, and there are known nematodes that do not respond to microtubule destabilization effects of benzimidazoles for one reason or another. Especially in cases of late-stage cancer, metastasized tumor resistance may develop rapidly, resulting in reversal of tumor shrinkage and relapse. Resistance to anthelmintic and possibly anti-tumor effects of benzimidazoles are most likely due to multiple mechanisms including single nucleotide polymorphisms at the beta-tubulin gene that develop over time during anti-parasitic treatment protocols. Therefore, benzimidazole resistance is a real phenomenon that presents an obstacle for the therapeutic potential limiting the clinical effectiveness in shrinking malignant tumors.

Benzimidazoles (BZs) work in nematodes and have been suggested to be effective in tumor cells as anti-parasitic drugs that bind to nematode beta tubulin, a microtubule protein that is important in continued cell function. These drugs cause parasites to die subsequently due to microtubule toxicity. Benzimidazoles have been shown to act in an identical fashion on tumor targets, primarily binding to beta tubulin and causing tumor cells to die. (Mrkvova et al., 20.19; Molecules, 24: 2152).

Reported studies to date entirely focus on benzimidazole's "on-site" (i.e., on tumor targets) effects including destabilization of the microtubules (through binding to beta-tubulin), inhibition of metabolic pathways (blocking glucose transport and reuptake, interference with energy production), anti-proliferative activity (mitotic catastrophe, G2/M cell cycle arrest), and induction of apoptotic cell death (DNA damage, activation of P53-p21 pathway; induction of pro-apoptotic Bax protein) (Mrkvova et al., 2019, Molecules, 24: 2152). These effects are directed at primary and secondary tumor sites and are subject to the development of resistance with the mutation of cancer cells. Chemotherapy drugs already exist that interfere with the cytoskeleton and spindle apparatus of tumor cells by binding to the microtubules, thereby disrupting key cellular mechanisms, including mitosis. Taxanes and *vinca* alkaloids are approved chemotherapy agents and are already being used as treatment regimen. Use of these agents, however, can result in 1) toxicity linked to binding to tubulin of all cells, tumor and healthy alike (e.g., neurotoxicity and neutropenia) and 2) resistance development as a function of long-term treatment. Benzimidazoles in contrast to taxanes and *vinca* alkaloids seem to be more selective in their effects towards rapidly dividing, aggressive, and invasive cancer cells, including stage 4 cancer, mostly sparing the healthy host cells. However, they suffer developing resistance to direct effects on the tumor. Therefore, the industry lacks a solution to resistance development incorporating recruitment of off-target benzimidazole effects originating in the gut which work to reactivate the host immune responses to tumor cells.

SUMMARY OF THE INVENTION

A first aspect of the invention accordingly comprises a composition comprising:
a first variant comprising a first anti-parasitic agent, a second anti-parasitic agent different from the first anti-parasitic agent, and a gut microbiome modulating agent, wherein the first variant is for use in treating cancer; a second variant comprising the first anti-parasitic agent and the second anti-parasitic agent different from the first anti-parasitic agent, wherein the second variant is for use in treating cancer in combination with the gut microbiome modulating agent;
a third variant comprising the first anti-parasitic agent and the gut microbiome modulating agent, wherein the third variant is for use in treating cancer in combination with the second anti-parasitic agent; a fourth variant comprising the second anti-parasitic agent and the gut microbiome modulating agent, wherein the fourth variant is for use in treating cancer in combination with the first anti-parasitic agent; or a fifth variant comprising the gut microbiome modulating agent, wherein the fifth variant is for use in treating cancer in combination with the first anti-parasitic agent and the second anti-parasitic agent.

In certain embodiments, the first anti-parasitic agent comprises benzimidazole.

In certain embodiments, the second anti-parasitic agent comprises benzimidazole.

In certain embodiments, the first anti-parasitic agent comprises parbendazole.

In certain embodiments, the second anti-parasitic agent comprises oxfendazole.

In certain embodiments, the gut microbiome modulating agent comprises a plurality of chitin microparticles.

In certain embodiments, the gut microbiome modulating agent comprises a prebiotic.

In certain embodiments, the gut microbiome modulating agent comprises a probiotic.

A second aspect of the invention comprises a method of cancer treatment comprising: a) administering to a patient a first anti-parasitic agent; b) administering to the patient a second anti-parasitic agent different from the first anti-parasitic agent; and c) administering to the patient a gut microbiome modulating agent; wherein the first anti-parasitic agent and the second anti-parasitic agent are administered concurrently for a predetermined first period of time; and wherein the gut microbiome modulating agent is administered for a predetermined second period of time.

In certain embodiments of the method, the first anti-parasitic agent comprises benzimidazole.

In certain embodiments of the method, the second anti-parasitic agent comprises benzimidazole.

In certain embodiments of the method, the first anti-parasitic agent comprises parbendazole.

In certain embodiments of the method, the second anti-parasitic agent comprises oxfendazole.

In certain embodiments of the method, the parbendazole is administered at a dose of 5 mg/kg/day.

In certain embodiments of the method, the oxfendazole is administered at a dose of 5-9 mg/kg/day.

In certain embodiments of the method, the gut microbiome modulating agent comprises a plurality of chitin microparticles.

In certain embodiments of the method, the gut microbiome modulating agent comprises a prebiotic.

In certain embodiments of the method, the gut microbiome modulating agent comprises a probiotic.

In certain embodiments of the method, the predetermined first period of time is two weeks.

In certain embodiments of the method, the predetermined second period of time is two weeks.

In certain embodiments of the method, the method further comprises continuing administration of the first anti-parasitic agent and the second anti-parasitic agent concurrently with the gut microbiome modulating agent during the predetermined second period of time.

In certain embodiments of the method, the method further comprises ceasing administration of the first anti-parasitic agent and the second anti-parasitic agent during the predetermined second period of time.

In certain embodiments of the method, the first anti-parasitic agent is administered through an excipient selected from the group consisting of injectable liquid solutions, injectable liquid suspensions, solid oral compositions, liquid oral compositions, suppositories, eye drops, topicals, salves, inhalants, transdermal patches, and microparticles.

In certain embodiments of the method, the second anti-parasitic agent is administered through an excipient selected from the group consisting of injectable liquid solutions, injectable liquid suspensions, solid oral compositions, liquid oral compositions, suppositories, eye drops, topicals, salves, inhalants, transdermal patches, and microparticles.

In certain embodiments of the method, the gut microbiome modulating agent is administered through an excipient selected from the group consisting of injectable liquid solutions, injectable liquid suspensions, solid oral compositions, liquid oral compositions, suppositories, eye drops, topicals, salves, inhalants, transdermal patches, edible shakes, capsules, powders, and microparticles.

In certain embodiments of the method, a concentration of the first anti-parasitic agent in the excipient is from 0.1% to 75% by weight.

In certain embodiments of the method, a concentration of the second anti-parasitic agent in the excipient is from 0.1% to 75% by weight.

In certain embodiments of the method, the gut microbiome modulating agent is administered at a dose of 10-20 mg/kg/day.

Accordingly, it is an objective of the invention to provide a new cancer treatment.

It is a further objective of the invention to provide methods of treating an individual suffering from cancer.

It is yet another objective of the invention to provide methods of treating an individual suffering from cancer using a combination of anti-parasitic agents or compounds.

It is a still further objective of the invention to provide methods of treating an individual suffering from cancer using a combination of anti-parasitic agents or compounds which minimize or prevent tumor resistance.

It is a further objective of the invention to provide methods of treating an individual suffering from cancer using a combination of two anti-parasitic agents.

It is yet another objective of the invention to provide methods of treating an individual suffering from cancer using a combination of anti-parasitic agents, in combination with one or more compounds which increase or enhance microbial populations, specifically chitin micro particles.

It is a still further objective of the invention to provide methods of treating an individual suffering from cancer using a combination of anti-parasitic agents, in combination with one or more compounds which increase or enhance gut microbiota (i.e., chitin micro particles)

It is a further objective of the instant invention to provide methods of treating an individual suffering from cancer using a combination treatment of oxfendazole and parbendazole.

It is yet another objective of the instant invention to provide methods of treating an individual suffering from cancer using a combination treatment of oxfendazole and parbendazole, with microbiome modulating oral therapy (i.e., chitin microparticles).

It is a still further objective of the invention to provide methods of treating an individual suffering from cancer using a combination treatment of oxfendazole and parbendazole, with one or more compounds which increase or enhance gut microbiota (i.e., chitin microparticles)

It is a further objective of the invention to provide methods of treating an individual suffering from cancer using in combination oral regimen of oxfendazole (OFZ) and parbendazole (PBZ), delivered in conjunction with microbiome modulating oral therapy with chitin microparticles.

It is yet another objective of the invention to provide methods of treating an individual suffering from cancer using a combination oral regimen of oxfendazole (OFZ) and parbendazole (PBZ), delivered with chitin microparticles which modulate the gut microbiome and enhance the anti-tumor immune response.

It is a still a further objective of the invention to provide methods of treating an individual suffering from cancer using oxfendazole (OFZ) and parbendazole (PBZ), in a combination therapy for cancer treatment with concomitant gut modulating and immune-enhancing chitin microparticles, particularly targeting the late-stage tumors.

It is a further objective of the invention to provide a combination therapy to treat end-stage cancer and prevent relapse by initial tumor shrinking using an oxfendazole (OFZ) and parbendazole (PBZ) combination oral treatment to cause a "negative pressure" release on the immune system. As the tumor size shrinks at the earlier phase of the treatment, the proliferative rate of the tumor cells will be decelerated, causing the likelihood of resistance-causing mutations in the beta tubulin gene to be decreased.

It is still a further objective of the invention to provide methods of treating an individual suffering from cancer using oxfendazole (OFZ) and parbendazole (PBZ), alone or in combination with gut microbiota modulating therapy using chitin microparticles in effective amounts to prevent cancer cell immunosuppression and remove the breaks on the immune system placed by the tumor.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

Various exemplary embodiments of the disclosed method will be described in detail with reference to the following drawings:

FIG. 10A shows a photograph of an OFZ-treated mouse with visible angiogenesis and tumor presence.

FIG. 10B shows a photograph of an OFZ-treated mouse with splenomegaly.

FIG. 10C shows a photograph of an OFZ-treated mouse with extensive metastasis and lung tissue damage.

FIG. 10D shows a photograph of an OFZ-treated mouse extensive metastasis in the lungs.

DETAILED DESCRIPTION OF THE INVENTION

Figure 1:
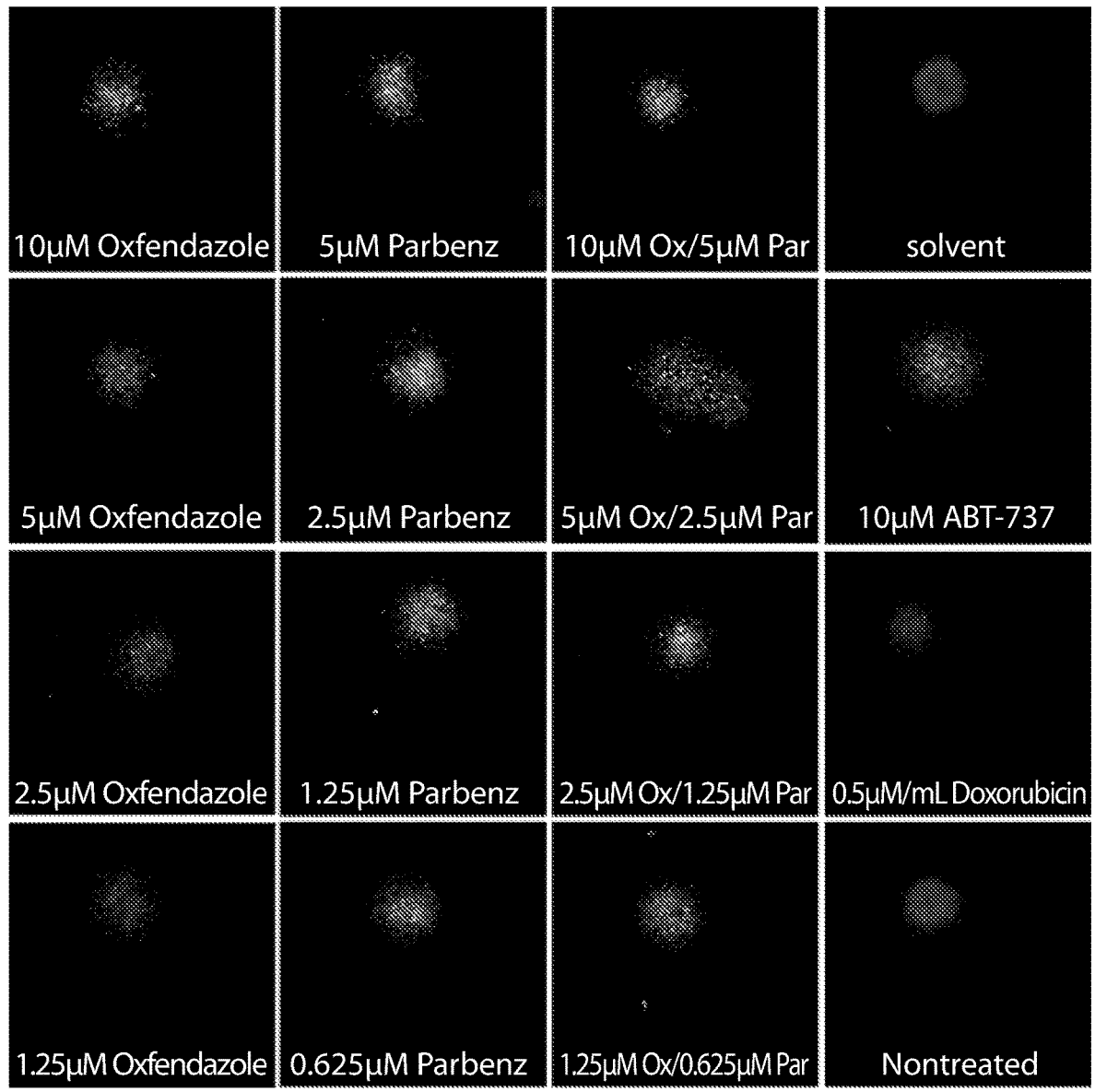
FIG. 1 shows three-dimensional spheroid multi-parametric assays using MDA-MB-468 cells treated with benzimidazoles and without treatment.

While the present invention is susceptible of embodiment in various forms, there is disclosed and will hereinafter be described a presently preferred, albeit not limiting, embodiment with the understanding that the present disclosure is to be considered an exemplification of the present invention and is not intended to limit the invention to the specific embodiments illustrated. Specific functional details disclosed herein are not to be interpreted as limiting, but merely as a basis for the claims and as a representation basis for teaching one skilled in the art to variously employ the present invention in virtually any appropriately detailed structure.

Disclosed is a novel combination therapy, preferably for the treatment of cancer including one or more anti-parasitic compounds or active agents, alone, or in combination with chitin microparticles which increase or enhance microbiota, preferably gut microbiota. The novel combination therapy includes an effective amount of anti-parasitic compounds or agents, such as parbendazole and oxfendazole, administered with a gut microbiome modulating oral therapy. In certain examples, the novel cancer combination therapy includes a combination oral regimen of oxfendazole and parbendazole, delivered with gut-modulating and anti-tumor immune response-enhancing chitin microparticles.

The invention describes a novel combination therapy for the treatment of cancer. The novel combination therapy for the treatment of cancer includes one or more anti-parasitic compounds or active agents, alone or in combination with one or more gut modulators. In certain examples, the gut modulators are chitin microparticles. As an illustrative example, the cancer treatment regimen comprises, in combination, effective amounts of anti-parasitic compounds, oxfendazole (OFZ) and parbendazole (PBZ), administered with a gut microbiome modulator oral therapy, preferably one or more compounds which increase or enhance gut microbiota. In certain examples, the novel combination therapy for the treatment of cancer comprises a combination oral regimen of oxfendazole (OFZ) and parbendazole (PBZ), concomitant with treatment with chitin microparticles.

The novel combination therapy for the treatment of cancer is believed to provide a treatment plan which re-targets medicines approved for veterinary applications on livestock, captive wildlife, and pets for anti-tumor effects in humans and devising a combination medicine treatment via co-administration of PBZ and OFZ for late-stage cancer patients and animal models with metastatic stage 4 cancer.

The novel combination therapy for the treatment of cancer provides a treatment plan applying a technique of slow downed hepatic clearance of benzimidazoles in general and OFZ in particular by way of co-administering PBZ, suppressing liver break down transiently and in a readily recoverable way, thereby expanding efficaciousness of anti-tumor outcome on primary and secondary tumor targets.

The novel combination therapy for the treatment of cancer provides a mechanism for resultant high plasma levels of benzimidazoles in general, and OFZ and its metabolites fenbendazole (FBZ) and fenbendazole-sulphone (FBZ-S02) to cross into the gut lumen and interact with host gut microbiota.

The novel combination therapy for the treatment of cancer provides a treatment plan in which high levels of benzimidazole, including OFZ, FBZ, or FBZ-S02, remain bioactive and available in the gut as a result of co-administration of PBZ, binding to microtubules of rapidly colonizing and invasive bacteria much in the same way as these compounds do to eukaryotic microtubules. Bacterial microtubules share high levels of identity with eukaryotic microtubules. Bacterial microtubules are smaller in diameter than their counterparts in eukaryotic cells but have the same basic architecture. Benzimidazoles have a preference towards rapidly dividing cells (such as tumor cells) or rapidly invading organisms (such as nematodes) as opposed to slow dividing cells or spreading organisms (such as host cells). In certain examples, the proposed treatment regimen slows down the kinetics of OFZ metabolism, expands the time window of treatment efficacy, and affords the elimination of immune suppressant bacterial colonies in the gut that are known to be aggressive, using the microtubule toxicity mechanism. This is the first step in the reactivation of the host immune system.

In certain examples, the novel combination therapy for the treatment of cancer provides a treatment plan including intermittent cycles of transient hepatic suppression by co-administering PBZ, OFZ, and chitin microparticles, eliminating aggressive bacterial colonies that suppress the peripheral and innate immune system of the host and sequentially enriching the immune-supporting bacterial colonies of the gut. The resultant shift in gut microbiota and subsequent re-activation of the host immune system with the ability to attack the tumor cells is proposed as the tipping point for prevention of benzimidazole resistance development towards anti-tumor effects.

In certain examples, the novel combination therapy for the treatment of cancer provides a treatment plan in which OFZ and PBZ co-administration expands the benzimidazole action in the body by generating two additional benzimidazoles with microtubule destabilizing capabilities: FBZ and FBZ-S02. Following this treatment regimen, both will be amply detected in plasma. This allows tumor cell death and elimination of "bad" bacteria to be mediated by multiple benzimidazoles simultaneously.

In other examples, the novel combination therapy for the treatment of cancer provides a treatment plan in which OFZ+PBZ, acting by themselves or through gut microbiota enhancement therapy, remove the breaks on the immune system placed by the tumor. Tumor growth is associated with immunosuppression. Cancer cells cause immunosuppression partly via activating different immune checkpoint pathways. Immune checkpoints are normal host mechanisms by which immune responses are regulated by way of suppressing the immune system after successfully eliminating pathogens. Tumor cells hijack these mechanisms to escape from host immune reactivity and attack by utilizing these check points. Examples of immune checkpoints include PD-1/PD-L1 and CTLA4.

As used herein, a pharmaceutically acceptable component/carrier etc. is one that is suitable for use with humans and/or animals without undue adverse side effects (such as toxicity, irritation, and allergic response) commensurate with a reasonable benefit/risk ratio and destabilizing capabilities, for example, FBZ and FBZ-S02. Following this exemplary treatment regimen, both FBZ and FBZ-S02 will be amply detected in plasma. This also allows tumor cell death and elimination of "bad" bacteria to be mediated by multiple benzimidazoles simultaneously.

As used herein, the term "effective amount" is an amount of the compounds of the present invention effective to yield the desired therapeutic response.

The terms "patient," "subject," or "individual" are used interchangeably herein, and each refer to a mammalian subject to be treated, with human patients being preferred. In some cases, the methods of the invention find use in experimental animals, veterinary application, and the development of animal models for disease, including, but not limited to primates and rodents such as mice, rats, and hamsters.

Oxfendazole (OF2), (5-(phyenylsulphinyl)-18-benzimidazole-2yl) carmabic acid methyl ester, has a structure similar to that of albendazole used in humans. It is a broad-spectrum anthelmintic and currently marketed for use against lungworms and enteric helminths in beef livestock. Compared with albendazole, OFZ has demonstrated a longer plasma half-life in animals (approximately 8.5-11 hrs.), suggesting that OFZ might maintain effective concentrations in the body for a longer period of time. OFZ is also extremely well-tolerated with no known toxicity. Fenbendazole (FBZ) and OFZ are metabolically interconvertible. Therefore, following OFZ administration, FBZ and fenbendazole sulphone (FBZ-S02) are detected in plasma in addition to OFZ. OFZ is metabolized in the liver and is excreted in urine and feces (An et al., 2019, Antimicrobial Agents and Chemotherapy, 63).

Parbendazole (PBZ), N-(6-butyl-1H-benzimidazol-2-yl) carbamic acid methyl ester is a carbamate ester and a member of benzimidazoles. It is utilized in veterinary medicine as an anti-parasitic drug, especially in sheep. PBZ inhibits monoamine oxidase in animal nematodes. It reaches peak blood levels approximately 6-8 hours after oral administration. PBZ is a transient liver function suppressant, and therefore co-administration with other benzimadazoles will delay clearance of the anti-parasitic drug from the plasma. Within 2 weeks after cessation of treatment, liver function recovers fully (Lyons et al., 1974, American Journal of Veterinary Research, 35, 1065-70).

In certain examples, the co-administration of OFZ with PBZ is used to overcome benzimidazole's resistance to anti-parasitic effects. This application uses this strategy now for anti-tumor effects. In anti-parasitic treatment, PBZ co-administration results in transient delay in OFZ metabolism (Hennessy et al., 1992, J Vet Pharmacol Therap, 15, 10-18), thereby achieving the following: 1) increasing the length of the therapeutic time window for microtubule binding effects; 2) increasing the amount of the OFZ that is absorbed; 3) deriving multiple bioactive benzimidazoles, such as OFZ, FBZ, and FBZ-S02, from slow clearance of OFZ that also show elevated levels in plasma; 4) increasing levels of secretion of OFZ, FBZ, and FBZ-S02 in the gut; and 5) binding microtubules of rapidly colonizing and immune suppressing bacteria in the gut, thereby eliminating "bad bacteria" overgrowth, such as that of *Clostridium perfringens, Staphylococcus*, and *Escherichia coli*.

Regarding on-target effects in certain examples, delayed hepatic metabolism of OFZ with co-administration of PBZ results in elevated levels of FBZ and FBZ-S02 in addition to OFZ in the blood, all of which are bioactive microtubule inhibitors. As bioavailable benzimidazoles target microtubules of rapidly dividing cells, tumor cells are eliminated. Decreased tumor load has downstream effects on the immune system (Radwan, Hossain et al. 2015, J Cell Biochem 116(1): 102-114). Particularly, as tumor growth is associated with immune suppression due to infiltration of tumors by myeloid-derived suppressor cells which suppress the activity of T lymphocytes, decreased tumor load is expected to reduce suppressor cell infiltration and thus enhance immune response against the tumor (Fleming, Hu et al. 2018, Front Immunol 9: 398).

Regarding off-target effects in certain examples, delayed elimination of parent drug OFZ results in a rich span of benzimidazoles (OFZ, FBZ and FBZ-S02) to be secreted into the gut lumen due to high amounts detected in blood, allowing for ample interaction with rapidly multiplying and aggressive bacteria that are likely suppressive towards the host immune system. Effects on the immune system are two-fold. Due to a decrease in tumor load, suppressor cells are decreased. This allows the cell-mediated immunity to get back into action and kill tumor cells. Treatment with FBZ alone is known to attenuate TH2 response (Cai, Zhou et al. 2009, Immunol Cell Bio 87(8): 623-629). To effectively eliminate tumor cells, a TH1 immune response is required. In certain examples, attenuation of TH2 response favors a TH1 bias, eliminating residual tumor cells remaining after co-administration of OFZ and PBZ.

In certain examples, gut microbiota modulating chitin microparticles are administered, enhancing the role of gut microbiome on the tumor and immune system. Sustained, thorough, and effective tumor-killing function may be critically dependent on benzimidazole's ability to disinhibit the host immune system by its actions at off-target and long-range locations such as the gut. This slowly developing, yet additive effect is dependent on activity of the exogenous benzimidazole compound and its active metabolites in the gut for an extended period, increasing the opportunity to interact with the host's gut microbial community and causing a shift in the gut microbiota. Rapidly dividing tumors hijack the host immune system and condition or reprogram the immune cells to aid/promote the tumor growth by secreting various chemical molecules. Thus, the immune system is unable to destroy tumors effectively on its own. In certain examples, the present invention provides for 1) initial on-site tumor destabilization; 2) prevention of the development of resistance to microtubule toxicity in response to longer treatment plans; 3) modulating and equilibrating gut microbiota; and 4) reorienting the host innate and peripheral immune cells to target the tumor cells.

In additional examples, the addition of chitin microparticles in the treatment permits modulation of gut microbiota, as well as enriches and expands positive bacterial colonies. Further, treatment with chitin microparticles (CMPs) will enhance anti-tumor immunity by shifting from M2 to M1 phenotype in macrophages and TH2 to TH1 in T lymphocytes.

Any of the components of the novel combination therapy may be prepared as a pharmaceutical or pharmacological composition, as known to one skill in the art in light of the present disclosure. Typically, such compositions may be prepared as injectables, either as liquid solutions or suspensions; solid forms suitable for solution in, or suspension in, liquid prior to injection; tablets or other solids for oral administration; time release capsules; or in any other form currently used, including but not limited to eye drops, creams, lotions, salves, and inhalants. The use of sterile formulations, such as saline-based washes, by surgeons, physicians, or healthcare workers to treat a particular area in the operating field may also be particularly useful. In certain examples, compositions are delivered via microdevice, microparticle, or other known methods.

In other nonlimiting examples, the pharmaceutical compositions are sterilized. In other examples, the pharmaceutical compositions contain adjuvants, such as preserving, stabilizing, wetting, or emulsifying agents; solution promoters; pH buffering agents; salts for regulating the osmotic pressure; and buffers. In additional examples, the pharmaceutical compositions contain other therapeutically valuable substances. In certain examples, the compositions are prepared according to conventional mixing, granulating, or coating methods. In certain examples, the compositions typically contain active ingredient at a concentration ranging from 0.1% to 75% by weight, preferably 1% to 50% by weight.

EXAMPLES

The design of an illustrative embodiment of a treatment plan incorporates intermittent phases of elimination of bad bacteria followed by flooding of the gut with chitin microparticles to increase the colonization with immune-system-supporting, "good" bacteria. Alternatively, a more directed approach in gut bacterial colonization includes oral administration of pellets of a set of immune system supporting bacteria, prebiotics, probiotics, and other similar gut microbiota-shifting agents or therapies as described above.

The novel combination therapy may be used to treat end-stage cancer and prevent relapse. Initial tumor shrinking effects of the PBZ+OFZ combination oral treatment may create ideal conditions for the release of "negative pressure" on the immune system exerted by the aggressive, rapidly dividing tumor. As the tumor size shrinks at the earlier phase of the treatment, the proliferative rate of the tumor cells will be decelerated, decreasing the likelihood of resistance-causing mutations in the beta tubulin gene.

PBZ is a unique compound in that in addition to its efficacy to bind beta tubulin, it also inhibits monoamine oxidase, which acts to augment monoaminergic transmitters, such as serotonin. More than 90% of the body's serotonin is synthesized in the gut. Colonic enterochromaffin cells supply serotonin to the gut mucosa, lumen, and circulating platelets. Circulating platelets sequester serotonin from the GI tract, releasing it to promote homeostasis. For example, gut-derived serotonin is crucial for immune responses, and deregulations in serotonin can cause irritable bowel syndrome and inflammation. Therefore, when using the inventive treatment, PBZ will increase levels of serotonin in the gut by way of inhibiting its metabolism through monoamine oxidases and thereby alter the gut microbiota towards bacteria that are immune activating with anti-tumor metabolites and byproducts. PBZ permits enrichment of the gut of monoaminergic transmitters, causing a shift in diversity and richness of bacterial community. These conditions enhance the host immune system.

PBZ temporarily delays hepatic metabolism of benzimidazoles. Benzimidazoles are metabolized in the liver. PBZ delays hepatic metabolism and therefore causes a steady release of bioactive compounds, which reach the gut through enterohepatic circulation. For example, the PBZ+OFZ combination regimen will result in substantially increased concentrations of fenbendazole (FBZ, a bioactive benzimidazole with anti-tumor effects), OFZ and fenbendazole-sulphone (FBZ-S02; a bioactive benzimidazole-like compound) in plasma. Therefore, PBZ extends the efficacy of OFZ, FBZ, and FBZ-S02 when co-administered with OFZ, all of which have their own beta tubulin-binding efficacy and gut mucosal interactions. The gut is composed of bacteria that colonize and proliferate. Similar to eukaryotes, bacteria in the gut utilize beta tubulin for cell wall growth, chromosomal segregation, and organelle assembly.

Dysbiosis is accompanied by "bad" bacteria that exploit the host and overtake the "good" bacteria. This can have detrimental effects on host/host immune response and aid tumor growth. In certain examples, the novel combination therapy in accordance with the invention: 1) shifts the gut microbiome from dysbiosis back to equilibrium by way of destabilizing the microtubulin structure of rapidly growing colonies of "bad bacteria," hence allowing for growth of "good" bacteria; 2) increases initial tumor killing potency (on-site effects), 3) prevents resistance to develop to the initial tumor shrinking effects, 4) re-equilibrates the gut microbiota to engage the gut mucosal, innate, and peripheral immune systems of the host to independently target the tumor (off-target effects), 5) reduces host toxicity due to (3), and 6) puts the break on growth of the primary and secondary tumors.

The instant invention repurposes the veterinary medicines PBZ and OFZ in a combination therapy for cancer treatment along with chitin microparticles, particularly enhancing anti-tumor immune response and targeting the late-stage tumors. In certain examples, a first anti-parasitic agent is administered concurrently with a second antiparasitic agent for a first predetermined length of time. In other examples, the first anti-parasitic agent includes PBZ, and the second anti-parasitic agent includes OFZ. In additional examples, a gut microbiome modulating agent is administered following the first predetermined length of time for a second predetermined length of time. In other examples, the gut microbiome modulating agent includes chitin microparticles. In the exemplary embodiment, a late-stage cancer treatment plan includes multiple cycles: (A) targeting tumor cells and invasive gut bacteria by use of a combination of OFZ 5 mg/kg/day and PBZ 5-9 mg/kg/day for two weeks to delay hepatic metabolism and enable clearance of tumor cells and rapidly colonizing bacteria. The effective dose range for anti-tumor effects of OFZ is 3-8 mg/kg/day and PBZ is 5-9 mg/kg/day. The mechanism increases microtubule toxicity in cancer cells and rapidly growing bacteria, resulting in the reduction of tumor load and elimination of the immune suppressant gut microbiome. This step (A) is followed for a predetermined length of time, for example, two weeks, and results in tumor shrinkage and ablation of invasive gut microbiota Step (B) includes targeting tumor cells and immune supporting gut bacteria by use of an OFZ 5 mg/kg/day and one or more compounds which increase or enhance gut microbiota, such as chitin microparticle capsules for a predetermined amount of time such as two weeks for resumption of liver metabolism and beneficial recolonization. In certain examples, the dosage amount of OFZ and PBZ may be increased or decreased based on patient response. In other examples, the predetermined length of time may be longer or shorter depending on the stage of the tumor. In this embodiment, the chitin microparticles received would be two capsules per day. The mechanism provides enrichment of gut microbiome by the daily consumption of chitin microparticles for reactivation of the immune system. Step (B) may be followed for about two weeks and results in tumor shrinkage and ablation of invasive gut microbiota. In this embodiment, chitin microparticles provide modulation of gut microbiota and promote an anti-tumor immune response by a shift from M2 to M1 and from TH2 to TH1 response. In other examples, Step (B) includes concurrent administration of OFZ, PBZ, and chitin microparticles, while in further examples, Step (B) only includes administration of chitin microparticles, and the patient ceases taking OFZ and PBZ at the end of Step (A).

The exemplary treatment plan may include multiple cycles, such as 4-6 cycles of the combined OFZ and PBZ regimen intertwined with gut enrichment protocol in a patient-centered and individualized manner depending on factors such as advancement of tumor and patient general health. The exemplary treatment plan includes enriching the gut microbiota through the use of gut microbiota modulating agents, such as chitin microparticles, that are non-toxic and enhance the anti-tumor immune response. In alternative examples, the gut enrichment phase of the treatment cycle can be replaced by directed bacterial supplementation (pre-biotics or probiotics) specifically targeting replenishment of a limited set of bacteria with antitumor effects reported in the literature such as Propionibacteria, *S. enterica, L. casei, Lactobacilli* spp etc. (Vivarelli et al., 2019), or other gut microbiota-shifting agents or therapies as described above. Delayed clearance of OFZ with co-administration of PBZ results in elevated levels of OFZ's inhibitors. Moreover, delayed elimination of the parent drug results in OFZ, FBZ, and FBZ-S02 to be secreted into the gut lumen due to the high amounts present in plasma, allowing for ample interaction with microtubules of rapidly multiplying and invasive bacteria that are likely suppressive toward the host immune system. Therefore, rapid, on-target effects of combination drug treatment (i.e., microtubule destabilization of cancer cells) are followed by more critical off-target effects (i.e., peripheral, innate, gut mucosal immune system activation of the host). The latter is the required component for prevention of benzimidazole resistance throughout the chronic treatment needed for complete elimination of tumor cells without relapse. Therefore, treatment with OFZ and PBZ can attenuate the TH2 immune response and could promote the TH1 response that is better able to eliminate tumor cells due to the off-target, gut-mediated reactivation of host immune responses.

In an example wherein a tumor mode is used to assess the treatment regimen, an aggressive breast cancer model shows the tumor to metastasize to the lungs by 3 weeks after tumor cell implantation, to the brain by 5 weeks post-tumor cell inoculation, and later requiring euthanasia. This is a treatment option for late stage, terminal cancer from repositioning two anthelmintic BZs (i.e., OFZ and PBZ) administered in combination with chitin microparticles, all of which have no side effects. Chitin microparticles (CMPS) are utilized to treat Irritable Bowel Syndrome in countries like Japan, and their anti-inflammatory effects are very well documented. Published data on oral administration of CMPs in breast cancer tumor-bearing mice showed downstream anti-inflammatory effects in the host peripheral immune system with ultimate end points of decelerating cancer growth and metastasis. CMP treatment is to enrich the immune-supporting bacterial colonies in the gut as well as shift the immune response to M1/TH1, leading to reduction of the M2 macrophage-tumor cell hybrids. The resultant shift in gut microbiota from baseline to a more diverse state following CMP treatment will be instrumental in onset of gut-peripheral signaling that activates the host immune system against the tumor cells. Therefore, in certain examples, a comprehensive pharmacological treatment is used incorporating on-target (i.e., tumors) and off-target (i.e., gut microbiome/TH2 to TH1 shift by the peripheral immune system) effects towards elimination of the tumor using concerted actions of exogenous benzimidazoles and the host immune system. A triple negative and aggressive breast cancer model [4T1Br4] was selected for brain metastasis to test the efficacy of this treatment plan at most advanced stages of the disease. The effectiveness of oral therapy combining repurposed benzimidazoles (BZs) that directly target the tumor cells (Oxfendazole, OFZ and Parbendazole, PBZ), in conjunction with chitin microparticles (CMPs) that regulate gut microbiome and downstream immune responses to indirectly inhibit tumor growth and metastasis was evaluated. This one-two punch method maximizes anti-tumorigenic effects whilst suppressing resistance to such therapy from developing in a chronic treatment regimen.

Dysbiosis is often seen in cancer patients impacting their overall health by altering the host immune response, host inflammation, and promoting metastasis and development of resistance to chemotherapeutics (Wang, J. et al. 2020; Buchta Rosean, C. et al. 2019; and Sheflin, A. M. et al., 2014). Gut dysbiosis increases intestinal permeability (Thevaranjan, N., et al. 2017) and could compromise intestinal epithelium. Intestinal epithelial cells (IECs) and the mucus layer provide physical barriers from intestinal lumen to tissue. IECs also play an immunoregulatory role through secretion of antimicrobial peptides, cytokines, and chemokines. Compromised IEC could result in translocation of microbes (Puppa, M. J., 2011) and thereby promote a systemic inflammatory response. The effect of dysbiosis on the immune system outside the gut was also shown to polarize macrophages from M1 to M2 phenotype in an airway inflammation model (Kim, Y. G., et al 2014). The role of the microbiome in response to cancer therapy demonstrates the influence of gut microbiome on the efficacy and toxicity of cancer therapeutics. (Inamura, K., et al 2021, Gopalakrishnan, V., et al., 2018, Routy, B. et al., 2018, and Matson, V., et al. 2018). Therapeutic responses to drugs can be either enhanced or reduced depending on microbial composition in the gut. Restoring the gut microbiome could be a strategy to enhance efficacy of chemotherapeutics. Therefore, the gut as a distal organ is critical in promotion of tumor growth and metastasis, and conversely may be further impacted from such inflammatory disease progression.

Macrophages play a critical role in tumor progression and polarization to either M1 or M2 type is dependent on cytokine microenvironment in the tumor during cancer progression; for example, M1 macrophages (pro-inflammatory) are anti-tumorigenic while M2 macrophages (anti-inflammatory) are pro-tumor growth. The role of macrophages, especially M2, has been revisited recently in the context of metastasis. M2 macrophages have been shown to form hybrids with tumor cells providing a "disguise" to the tumor cells such that they freely migrate and colonize other tissues in accelerating metastasis by evading the immune system. Further, macrophage-tumor cell hybrids are linked with radio resistance, drug resistance, high invasion abilities, and poor prognosis in cancer patients. Shibata et al. and others have shown that chitin (1-10 μm), a natural compound found in fungi and exoskeleton of crustaceans, induces activation of M1 type macrophages regulating both innate and adaptive immunity with production of cytokines that provide host resistance to microbial infections (Shibata, Y., et al. 1997, Lee, C. G., et al. 2008, Da Silva, C. A. et al., 2009). Nagatani et al. reported that treatment with chitin microparticles (CMPs), modulates the microenvironment in the gut and controls intestinal inflammation (Nagatani, K., et al 2012). Modulation of gut microbiota to restore good bacteria could alter short chain fatty acid (SCFAs) by products which could shift immune system from proinflammatory to anti-inflammatory.

Triple negative breast cancers—the collective term for breast cancers that do not express estrogen receptor (ER), progesterone receptor (PR), or the human epidermal growth factor receptor type 2 (HER 2)—are resistant to most types of targeted therapies. Triple negative breast cancer is sometimes described as being basal type, based on the resemblance of these cancer cells to the basal cells that line the breast ducts, although the cancer does not necessarily arise from these cells. Triple negative breast cancer also encompasses the claudin-low tumors, which have properties similar to those of stem cells. About 10-20% of breast cancer diagnoses in the US are of triple negative breast cancer. The MDA-MB-231 cell line used in this study has been classified as claudin-low, while the MDA-MB-468 cell line also used in this study has been classified as basal. Both of these cell lines show an invasive phenotype in vitro and are tumorigenic in vivo.

Treatment with CMPs will enhance anti-tumor immunity by shifting from M2 to M1 phenotype and in macrophages and TH2 to TH1 in T lymphocytes. Thus, in certain examples the inventive treatment includes CIP treatment to enrich the immune-supporting bacterial colonies in the gut as well as shift the immune response to M1/TH1, leading to reduction of the M2 macrophage-tumor cell hybrids. The resultant shift in gut microbiota from baseline to more diverse states following CMP treatment will be instrumental in onset of gut-peripheral signaling that activates the host immune system against the tumor cells. Therefore, the invention utilizes a comprehensive pharmacological treatment incorporating on-target (i.e., tumors) and off-target (i.e., gut microbiome/TH2 to TH1 shift by the peripheral immune system) effects towards elimination of the tumor using concerted actions of exogenous BZs and host immune system. In certain nonlimiting examples, CMPs are ingested in an amount ranging from 10-20 mg/kg/day. Examining the triple negative and aggressive breast cancer model [4T1Br4] selected for brain metastasis to test the efficacy of this treatment plan at most advanced stages of the disease, it is expected that treatment with CMPs reduces local and peripheral inflammation through their effect on the gut and by shifting macrophage phenotype from M2 to M1 type. The calming effect of CMPs on intestinal inflammation was shown to provide gut epithelial integrity, prevent leakage of gut microbes into periphery, and dampen peripheral inflammation. Thus, reduction in metastasis observed in the murine model of breast cancer is due not only to macrophage polarization but also to CMP's effects on the gut microbiome and SCFAs, as well as subsequent cross talk with the host inflammatory response.

The data presented show evidence for reducing tumor growth with OFZ/PBZ dual treatment and the effectiveness of combination CMP and BZ treatment in significantly reducing tumor metastasis in the aggressive, rapidly metastasizing 4T1Br4 BALB/c mouse model.

Referring to the figures, FIG. 1 shows an exemplary in vitro assay where MDA-MB-468 cells which were allowed to form a spheroid overnight were treated for 24 h with 10, 5, 2.5, or 1.25 μM Oxfendazole, 5, 25, 1.25 or 0.625 μM PBZ or a combination 10/5, 5/2.5, 2.5/1.25 or 1.25/0.625 μM OFZ/PBZ. Controls included 10 μM ABT737, 5 μg/mL 5-fluorouracil, 0.5 μg/mL doxorubicin, media alone, and solvent controls. After treatments, cells were labeled with the cell permeable nuclear stain Hoechst 33342, a marker for cleaved caspase 3/7, and the cell impermeable nucleic acid stain 7AAD for three hours. Cells were fixed then images acquired using a high content imager at 10× magnification. Scale bars represent 200 μm. The experiment was repeated 3 times. The results show the combination of OFZ/PBZ yielded increased numbers of cancer cell death, as shown in Column 3, compared to single treatments, as shown in Columns 1 and 2. No cell death was observed in controls, as shown in column 4.

MDA-MB-231 or MDA-MB-468 cells were plated on a black plate with clear bottom low adherence spheroid 384-well tissue culture plate (Corning 3830; Corning NY) at a concentration of 1,500 cells per well in ice-cold complete media without phenol red containing 2.5% matrigel (BD Biosciences, Billerica, MA) in a final volume of 30 µL/well and allowed to adhere for 24 hours. After confirming the formation of a spheroid, 30 µL of medium containing treatment at two times the final concentration was added. Treatments consisted of 10, 5, 2.5 or 1.25 µM oxfendazole (OFZ), 5, 2.5, 1.25 or 0.625 µM parbendazole (PBZ) or a combination 10/5, 5/2.5, 2.5/1.25 or 1.25/0.625 µM OFZ/PBZ. Controls included 10 µM ABT737, 5 µg/mL 5-fluorouracil, 0.5 µg/mL doxorubicin, media alone, and solvent controls. Solvent for drug treatments was 10% DMSO by weight. Cells were incubated with treatment for 24 h. At the end of this incubation 20 µL/well of a staining mixture containing 2 drops/mL NucBlue Live Cell Stain Hoechst 33342 (Molecular Probes, Eugene, OR), 5 µM CellEvent™ Caspase-3/7 Green Detection Reagent (Molecular Probes, Eugene, OR) and 100 g 7-amino-actinomycin D (7AAD; Sigma, St. Louis, MO) were added and allowed to incubate for 3 h. Cells were fixed with 4% paraformaldehyde by weight. Images were acquired using the ImageXpress® Micro XLS widefield HCS (Molecular Devices, Sunnyvale, CA), with a 10× Plan Fluor objective, binning at 2 and focusing on plate bottom, then offset by bottom thickness. A stack of 8 images separated by 10 µm starting at the well bottom and covering approximately the lower half of each spheroid were acquired. The best focus projection of this stack was analyzed using the Multi-Wavelength Cell Scoring Module of the MetaXpress 5.1.0.3 software (Molecular Devices, Sunnyvale, CA). The results were plotted using Microsoft excel (Redmond, WA). To normalize results, the solvent control values were subtracted from the 7AAD and the Caspase 3 percent positive results for treatment samples. Total cell count was expressed as a percentage comparing treatments to respective solvent controls. Compounds were tested in duplicate within plates. The in vitro effectiveness of BZs, either singly or in combination on tumor cytotoxicity using MDA-MB468 human breast cancer cell line spheroids was assessed.

Figure 2:
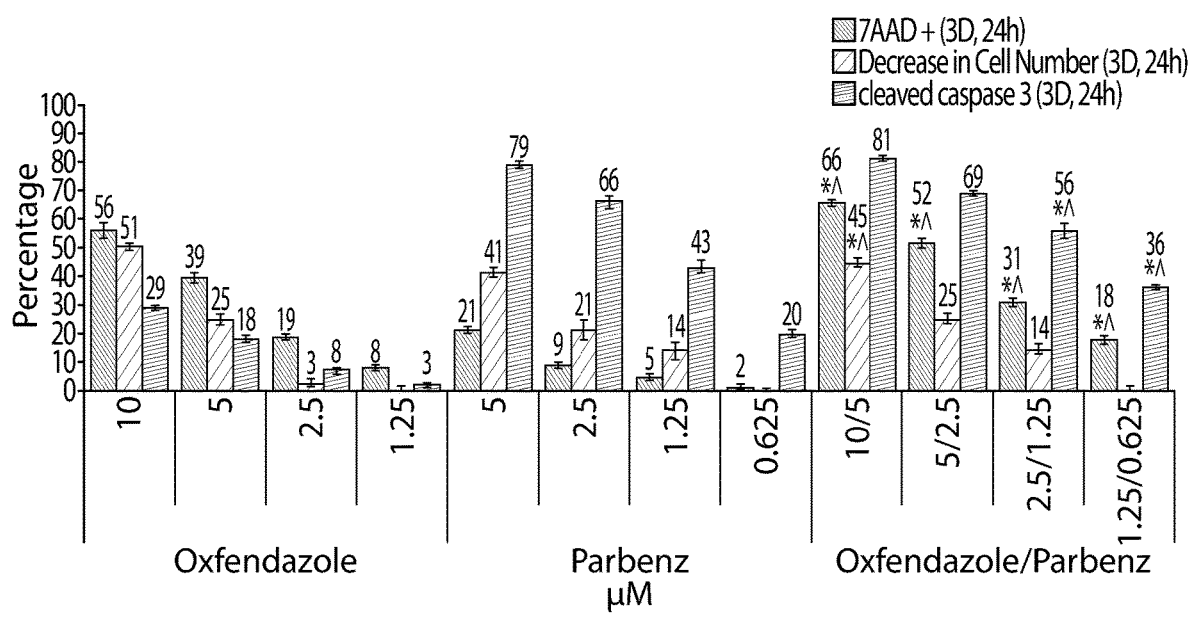
FIG. 2 shows a graph of observed MDA-MB-468 cell death using oxfendazole (OFZ), parbendazole (PBZ), and an OFZ/PBZ combination.

The results from the analysis of the images for the three independent in vitro experiments were averaged and graphed and are shown in FIG. 2. Analysis of images shows that both compounds were active in this cell line, with oxfendazole (OFZ) favoring death by loss of membrane integrity while parbendazole (PBZ) caused more caspase cleavage. PBZ was statistically significantly more potent than OFZ. The combination of OFZ/PBZ worked statistically significantly better than either of the drugs alone with more induction of death by loss of membrane integrity at all concentrations and an increase in caspase cleavage at the lower concentrations. The graph in FIG. 2 shows the average of the results from three independent experiments±standard deviation.

Figure 3:
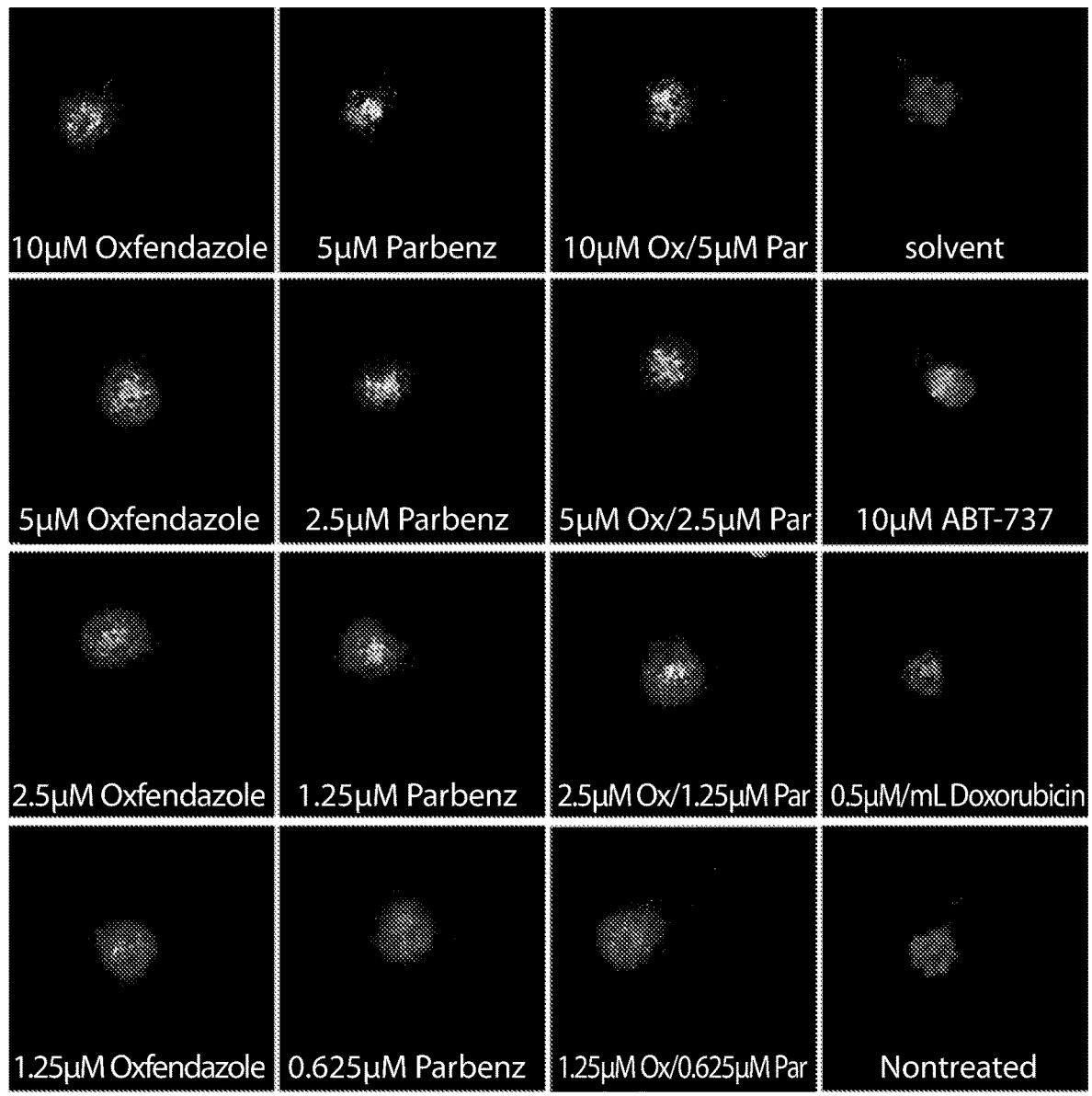
FIG. 3 shows three-dimensional spheroid multi-parametric assays using MDA-MB-231 cells treated with OFZ, PBZ, an OFZ/PBZ combination, and no treatment.

FIG. 3 illustrates the in vitro effectiveness of BZs, either singly or in combination on tumor cytotoxicity using MDA-MB4231 human breast cancer cell line spheroids. MDA-MB-231 spheroids were treated as stated in the methods for 24 hours. At the end of this incubation, spheroids were stained, fixed and images were acquired using a high content imager. Three independent experiments were performed. The images from one representative experiment are shown in FIG. 3. Images were analyzed to determine cell counts based on DNA (Hoechst 33342 stain; blue), those dying through apoptosis by following cleavage of caspase 3, and cells dead or dying as measured by the loss of their membrane integrity (7-aminoactinomycin; red). MDA-MB-231 cells were allowed to form a spheroid overnight, then were treated for 24 h with 10, 5, 2.5, or 1.25 µM Oxfendazole (OFZ), 5, 2.5, 1.25 or 0.625 µM Parbendazole (PBZ) or a combination 10/5, 5/2.5, 2.5/1.25 or 1.25/0.625 µM OFZ/PBZ. Controls included 10 µM ABT737, 5 µg/mL 5-fluorouracil, 0.5 µg/mL doxorubicin, media alone, and solvent controls. After treatments, cells were labeled with the cell permeable nuclear stain Hoechst 33342, a marker for cleaved caspase 3/7, and the cell impermeable nucleic acid stain 7AAD for three hours. Cells were fixed then images acquired using a high content imager at 10× magnification. Scale bars represent 200 µm. The experiment was repeated 3 times.

Figure 4:
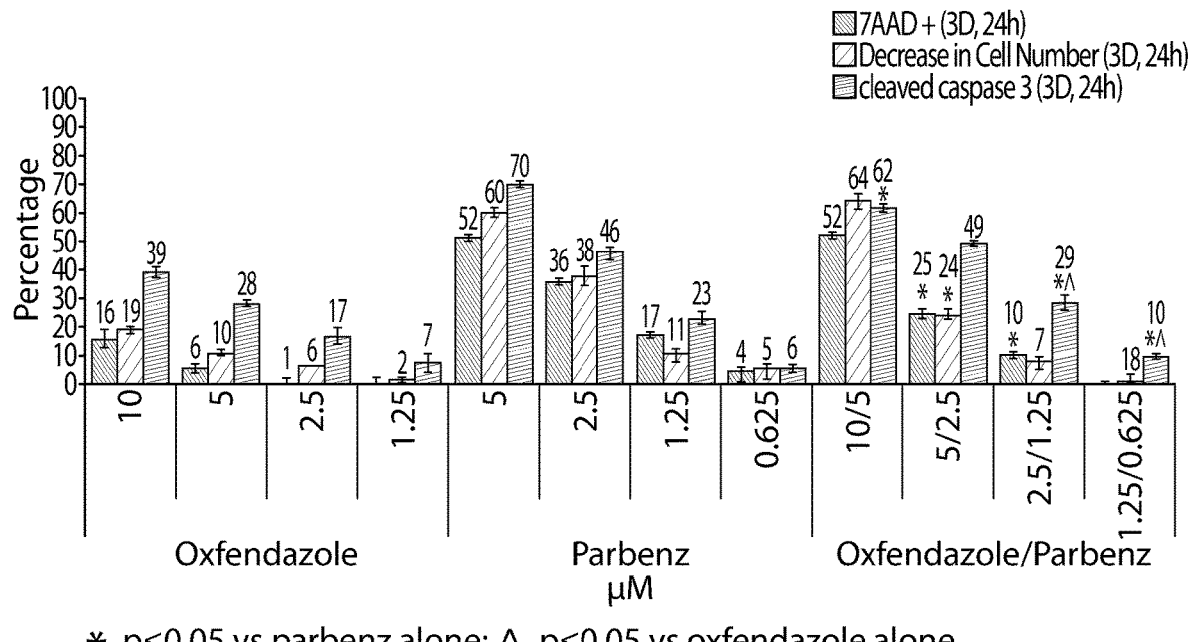
FIG. 4 shows a graph of observed MDA-MB-231 cell death using oxfendazole (OFZ), parbendazole (PBZ), and an OFZ/PBZ combination.

FIG. 4 shows results from the analysis of the images for the three independent in vitro experiments, averaged and graphed. Analysis of the images shows that while both compounds were active in this cell line, OFZ exhibited a more modest activity than the one seen with the MDA-MB-468 cells. PBZ was statistically significantly more potent than OFZ. The graph shows the average of the results from three independent experiments±standard deviation. The results show that while both compounds showed activity in a dose dependent manner, the activity of OFZ was more modest in this cell line compared to the MDA-MB-468. In contrast, PBZ was statistically significantly more potent at the concentrations tested than OFZ. In this cell line, both treatments caused caspase cleavage suggesting the induction of apoptosis.

Figure 5:
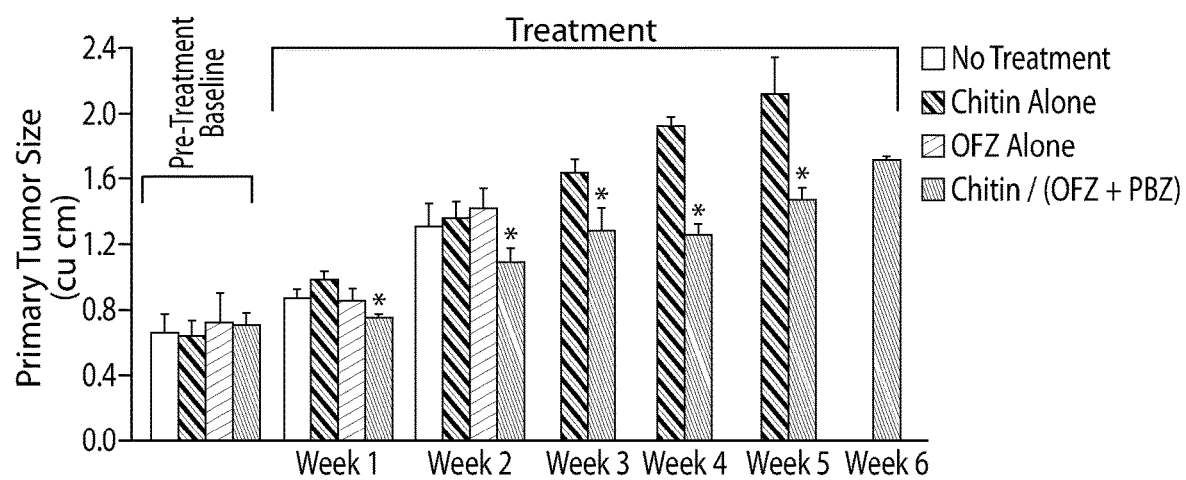
FIG. 5 shows a graph of primary tumor size measured biweekly and average tumor size (in cu cm) plotted for pre-treatment baseline and across anti-cancer treatment weeks.

FIG. 5 shows an exemplary in vivo study with a developed triple negative and aggressive breast cancer model [4T1Br4; Kim et al., 2018; Dis Model Mech, 11] that is selected for brain metastasis to test the efficacy of this treatment plan at most advanced stages of the disease. Light to ten-week-old BALB/c mice (Charles River Laboratories; total of 48 mice) are orthotopically injected with 25,000-50,000 4T1Br4 mammary tumor cells in 100 microliters unilaterally into 4th mammary fat pad. Primary tumor growth was monitored by caliper measurements and biweekly body weight and wellness checks. When tumor size reached 0.5-0.7 cu cm, animals were divided into 4 experimental groups: 1) No Treatment (n=8), 2) Single OFZ Treatment (n=8), 3) Single CMP Treatment (n=16), 4) Combination CMP and OFZ/PBZ Treatment (n=16). Treatments started at 2 weeks post cancer cell inoculation. The following are the oral gavage doses: OFZ, 5 mg/kg; PBZ, 9 mg/kg; FBZ, 10 mg/kg; CMPs 10 mg/kg. All drugs are dissolved in sterile saline and final gavage volume is 200 microliters per mouse. OFZ and PBZ doses match the best doses reported in veterinary use for anti-parasitic end points (Hennessy et al. 1985, J Vet Pharmacol Ther, 8: 270-275). When primary tumors reach 1 cu cm, they were excised under general anesthesia for all groups except for half of the animals in single CMP and combination CMP and BZ treatments. For those groups, half of the animals in each of these drug treatments received tumor excision surgery and for the remaining half, the primary tumors are untouched throughout the course of the experiment. Primary tumor size, percentage tumor growth compared to pre-treatment baseline, body weights and survival were assessed. Upon death, necropsy was conducted to assess metastatic tumor growth in distal organs. Regarding the chart shown in FIG. 5, primary tumor size was measured by a caliper biweekly and average tumor size (in cu cm) was plotted for pre-treatment baseline and across anti-cancer treatment weeks. Treatment started 2 weeks past orthotopic cancer cell inoculation. The dotted line indicates primary tumor excision surgery for OFZ, No Treatment, and one half of Chitin Alone and one half of Chitin/(OFZ+PBZ) treatment groups. The other half of Chitin Alone and Chitin/(OFZ+PBZ) groups continue the treatment without surgical removal of the primary tumor. Values are represented as means+SEMs. During pre-treatment, all mice have comparable primary tumor size, and no group differences are detected. Within the first week of oral gavage treatment, the oral Chitin/(OFZ+PBZ) combination treatment group showed a significant deceleration in primary tumor growth. The suppressed primary tumor growth is apparent throughout the entirety of treatment regimen in combination CMP/dual BZ treatment group.

Figure 6:
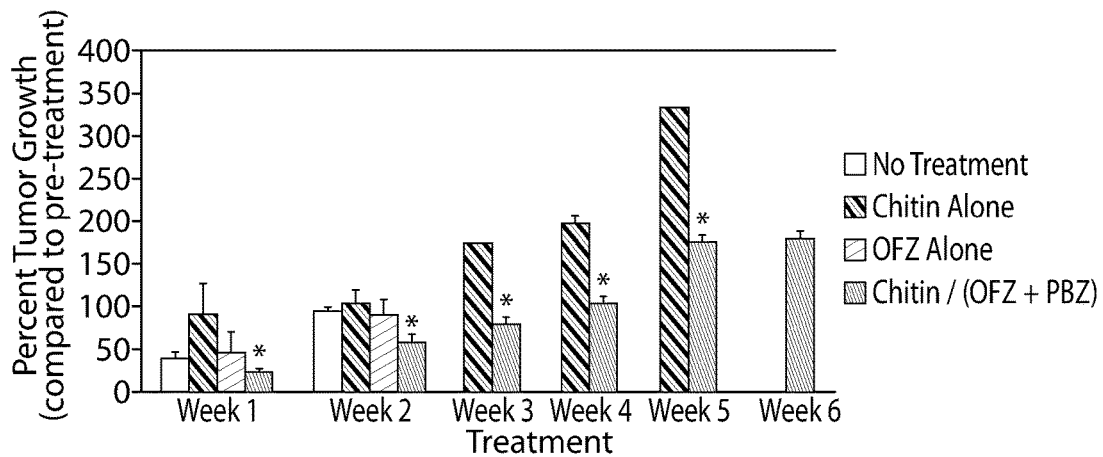
FIG. 6 shows a graph of percent tumor growth calculated from pre-treatment tumor size baseline across 6 weeks of anti-cancer treatments.

FIG. 6 shows percent tumor growth calculated from pre-treatment tumor size baseline across 6 weeks of anti-cancer treatments and plotted weekly. Treatment started 2 weeks post-cancer cell inoculation. The dotted line indicates the tumor excision surgery for all mice except one half of the experimental groups for Chitin Alone and Chitin/(OFZ+PBZ) groups. One half of the animals in these two groups continued treatment regimen without removal of primary tumors. Data are represented as group averages+SEMs. Chitin/(OFZ+PBZ) group showed significantly lower breast tumor growth across treatment weeks compared to other groups.

Figure 7:
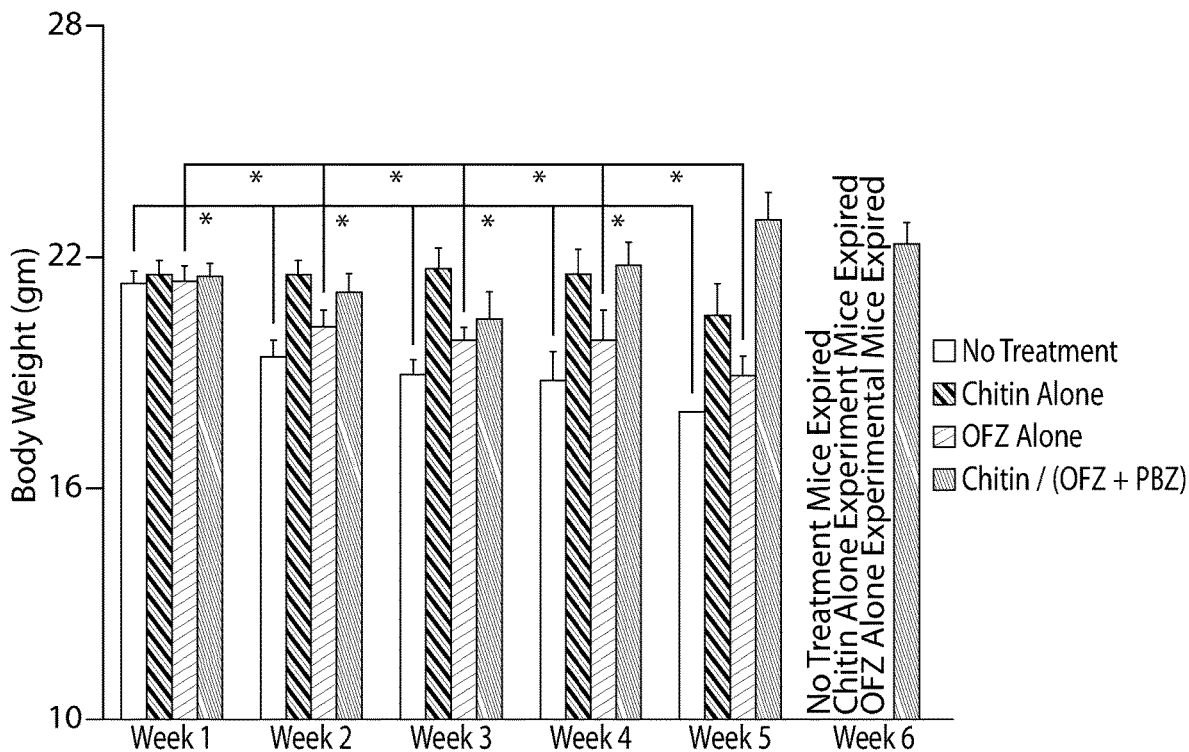
FIG. 7 shows a graph of body weight (gm) measurements taken biweekly across treatment weeks for all mice in four experimental groups.

FIG. 7 shows a graph of body weight (gm) measure taken biweekly across treatment weeks for all mice in the four experimental groups. Measures were averaged for each week and represented as Means+SEMs. Treatment started two weeks post-inoculation with cancer cells. No Treatment and Single OFZ treatment groups showed significant decline in bodyweight measurements, noticeable as early as 2 weeks into treatment. Chitin Alone and Chitin/(OFZ+PBZ) groups maintained body weight across treatment weeks without decline. By week 6, all mice in No Treatment, Chitin Alone and OFZ Alone groups deceased due to disease endpoints. The only group that had animals surviving at 6th week of treatment was the Chitin/(OFZ+PBZ) group (n=7 remaining).

The data collected during the live animal work on mice bearing an aggressively metastatic form of the triple negative breast cancer (4T1Br4) show that oral treatment with CMP in combination with dual BZs (OFZ+PBZ) produced the most anti-tumor effects compared to single OFZ or single CMP treatments or mice that received no treatment at all. These effects were deceleration of the primary tumor growth and prevention of health and wellness decline across 6 weeks of treatment (8 weeks from cancer cell inoculation), and improvement in survival of mice at late-stage cancer time points.

Figure 8A:
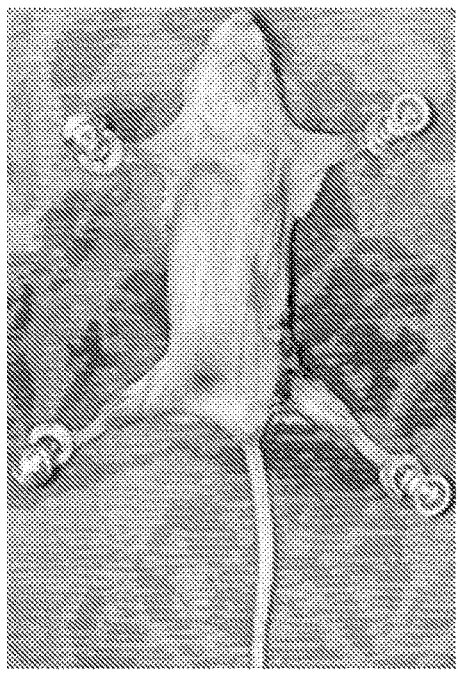
FIG. 8A shows a photograph of a no-treatment mouse with visible angiogenesis.
Figure 8B:
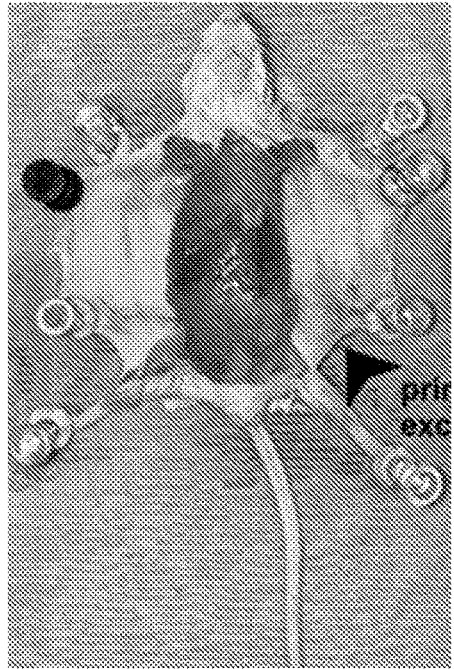
FIG. 8B shows a photograph of a no-treatment mouse with splenomegaly.
Figure 8C:
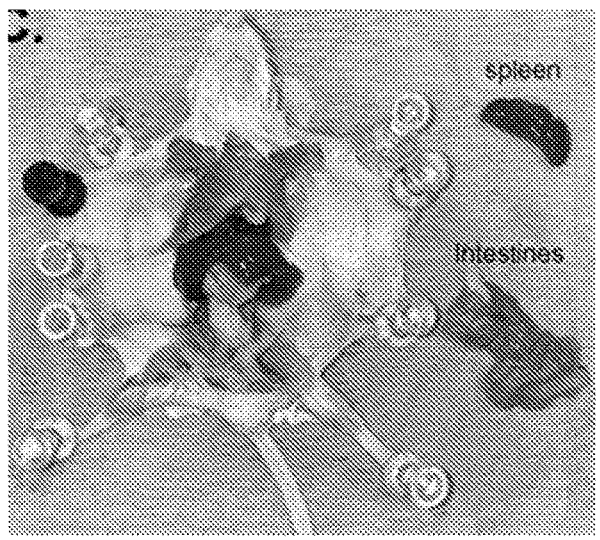
FIG. 8C shows a photograph of a no-treatment mouse with extensive metastasis and lung tissue damage.
Figure 8D:
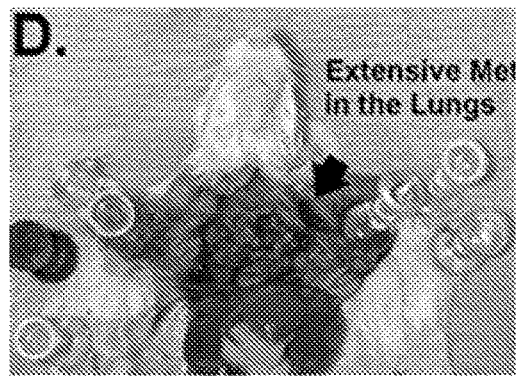
FIG. 8D shows a photograph of a no-treatment mouse with extensive metastasis in the lungs.

Necropsy was then conducted on the animals that expired for assessment of gross metastasis in lungs, brain and liver that may be responsible for expiration of mice. Detailed necropsy was performed and archived for each animal. FIGS. 8A-D show a representative No Treatment mouse that expired at 32 d post cancer cell inoculation due to labored breathing and loss of body weight. This timeline for expiration matches previously published timeline with the aggressively metastatic triple negative breast cancer model (i.e., 4TBr4; Kim et al., 2018; Dis Model Mech, 11). FIG. 8A shows a photograph of the mouse at two weeks post-inoculation, wherein the mouse received tumor excision surgery when the tumor was sized at 1 cu cm with a caliper. Angiogenesis is visible at excision site at this time point. FIG. 8B shows the same mouse where splenomegaly is observed. FIG. 8C shows extensive metastasis and lung tissue damage apparent upon opening the chest cavity of the mouse. FIG. 8D shows extensive metastases in the mouse lungs. In the No Treatment group, mice expired entirely due to lung metastasis.

Figure 9A:
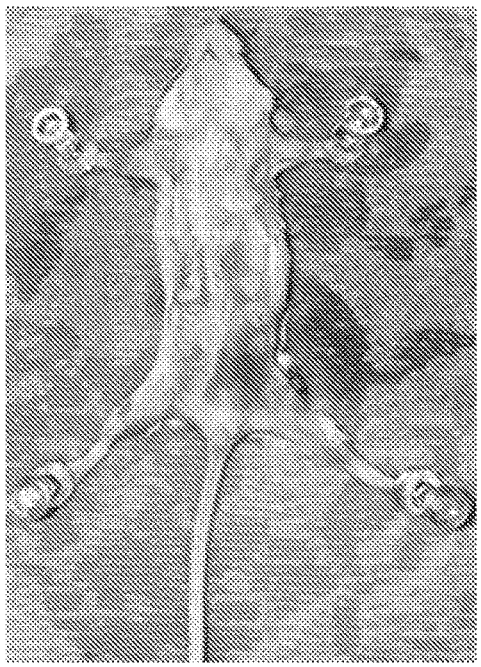
FIG. 9A shows a photograph of a chitin-treated mouse with no visible angiogenesis.
Figure 9B:
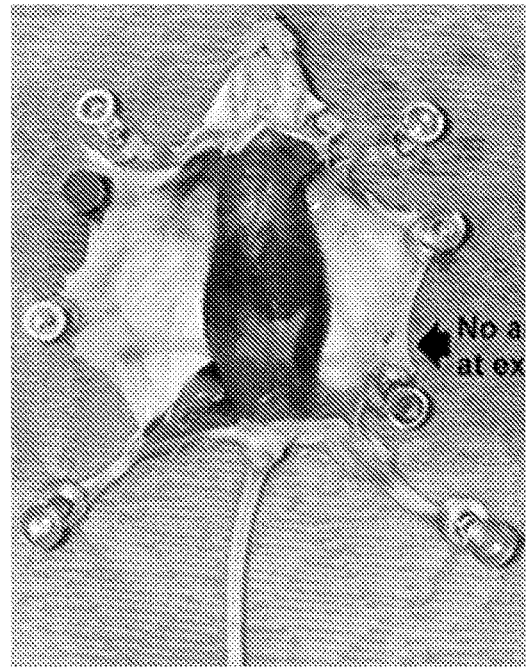
FIG. 9B shows a photograph of a chitin-treated mouse with splenomegaly.
Figure 9C:
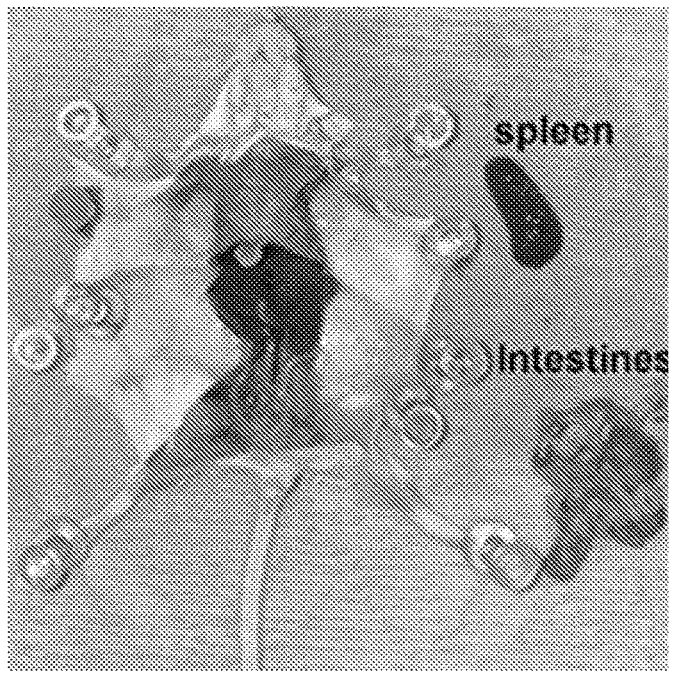
FIG. 9C shows a photograph of a chitin-treated mouse with extensive metastasis and lung tissue damage.
Figure 9D:
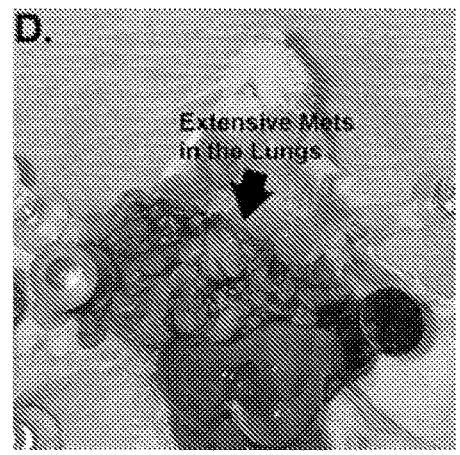
FIG. 9D shows a photograph of a chitin-treated mouse with extensive metastasis in the lungs.

FIGS. 9A-D show a photograph of a representative Chitin Alone mouse that expired at 36 d post cancer cell inoculation due to labored breathing. The mouse received cancer cell inoculation two weeks before oral treatment with Chitin started. FIG. 9A shows the mouse when the tumor is sized at 1 cu cm with a caliper two weeks past inoculation. No angiogenesis is visible at excision site at this time point. FIG. 9B shows instances of splenomegaly. FIG. 9C shows extensive metastasis and lung tissue damage apparent upon opening the chest cavity. FIG. 9D shows extensive metastases in the mouse lungs. In Chitin Alone group, mice expired entirely due to lung metastasis.

FIGS. 10A-D show a representative OFZ Alone mouse that expired at 32 d post cancer cell inoculation due to labored breathing and loss of body weight. OFZ treatment started 2 weeks post-cancer cell inoculation. At necropsy, a small mass is observed regrowing in the tumor excision site and angiogenesis is visible. FIG. 10A shows the mouse when the tumor is sized at 1 cu cm with a caliper two weeks past inoculation. FIG. 10B shows instances of splenomegaly. FIG. 10C shows extensive metastasis and lung tissue damage apparent upon opening the chest cavity. FIG. 10D shows extensive metastases in the mouse lungs. In the OFZ Alone group, mice expired entirely due to lung metastasis.

Figure 11A:
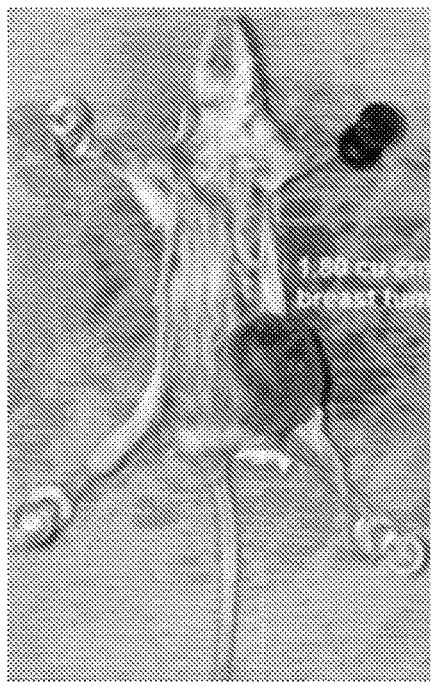
FIG. 11A shows a photograph of a combined chitin/OFZ+PBZ-treated mouse with visible angiogenesis and tumor presence.
Figure 11B:
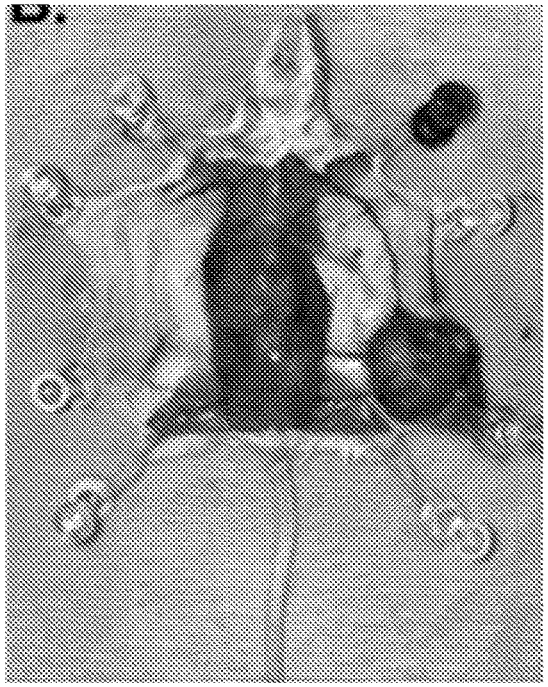
FIG. 11B shows a photograph of a combined chitin/OFZ+PBZ-treated mouse with no gross sign of lung metastasis.
Figure 11C:
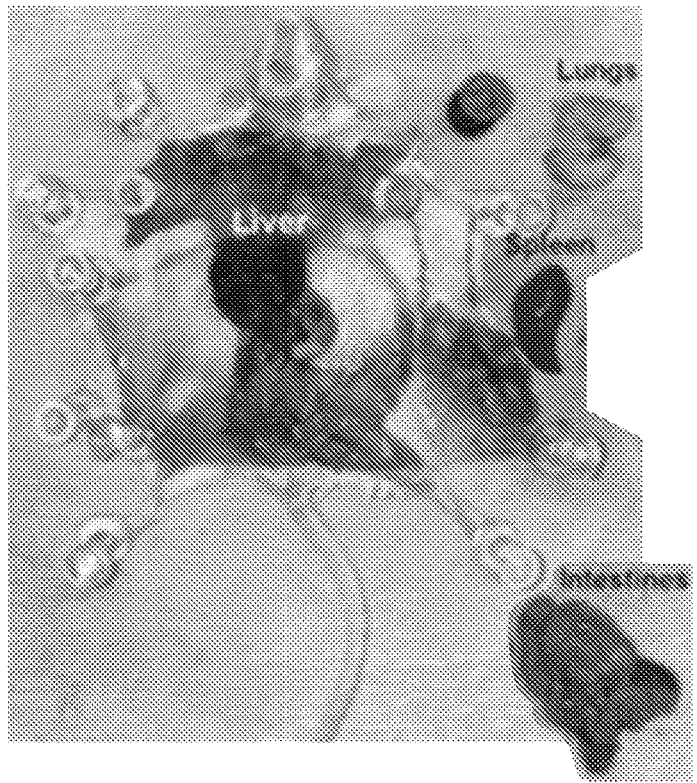
FIG. 11C shows a photograph of a combined chitin/OFZ+PBZ-treated mouse with brain tissue consistency and no sign of outward metastasis.
Figure 11D:
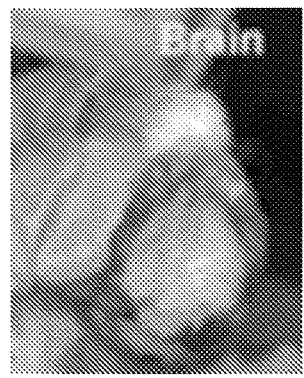
FIG. 11D shows a photograph of a combined chitin/OFZ+PBZ-treated mouse with minimum to no sign of lung metastasis.

FIGS. 11A-D show a representative Chitin/(OFZ+PBZ) mouse that was euthanized at 62 d post cancer cell inoculation due to inability to walk caused by a massive primary breast tumor. FIG. 11A shows the same mouse that did not receive primary tumor excision surgery. The mouse started receiving oral treatment at 2 weeks post cell inoculation. At necropsy, an active self-contained primary tumor is clearly visible with angiogenesis. FIG. 11B shows that when the chest cavity was opened for assessment of the lung tissue, no gross sign of lung metastasis was visible. FIG. 11C shows brain tissue consistency and that the mouse's outside appearance did not show signs of metastasis. FIG. 11D shows the Chitin/(OFZ+PBZ) group showed minimum to no sign of lung metastasis and therefore survived the latest time points. The animals expired mainly due to physical limitations caused by a massive primary tumor such as inability to move or groom, leading to a decline in body condition scores below levels required for survival. It is especially important to note that even though active primary tumor is evident in mouse that did not have their primary tumors surgically removed, the combination treatment was sufficient for suppressed metastasis.

Necropsy findings confirmed metastatic process in the lungs as cause of death in No Treatment, Chitin Alone and OFZ Alone treatment groups. In contrast, the decelerated primary tumor growth was associated with minimum to no metastases in the lungs in Chitin/(OFZ+PBZ) combination treatment group. This group of animals survived the longest and/or were euthanized because of other types of physical decline or injury due to oral gavage. In sum, CMP together with tumor cell selective toxicity of BZs (FIGS. 1-4) will prevent metastasis and reduce primary tumor load as evidenced by primary tumor measurements, body condition scores and survival across treatment weeks (FIGS. 5-11). This particular combination treatment with CMPs and dual BZs (OFZ+PBZ) leads to less complication-related, premature euthanasia and overall better body condition scores at check-up.

All patents or publications mentioned in this specification are indicative of the levels of those skilled in the art to which the invention pertains. All patents or publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments.

What is claimed is:

1. A method of treating cancer, comprising orally administering to a subject in need thereof a first anti-parasitic benzimidazole and a gut microbiome modulating agent, wherein the gut microbiome modulating agent comprises chitin microparticles.

2. The method according to claim 1, further comprising orally administering a second anti-parasitic benzimidazole different from the first anti-parasitic benzimidazole.

3. The method according to claim 1, wherein the first anti-parasitic benzimidazole is parbendazole or oxfendazole.

4. The method according to claim 2, wherein the first anti-parasitic benzimidazole is parbendazole and the second anti-parasitic benzimidazole is oxfendazole.

5. The method according to claim 1, wherein the gut microbiome modulating agent further comprises a probiotic.

6. The method according to claim 1, wherein the first anti-parasitic benzimidazole is administered for a first period of time that is two weeks.

7. The method according to claim 6, further comprising administering a second anti-parasitic benzimidazole different from the first anti-parasitic agent during the first period of time.

8. The method according to claim 6, wherein the gut microbiome modulating agent is administered for a second period of time that is two weeks.

9. The method according to claim 8, wherein the second period of time is subsequent to the first period of time.

10. The method according to claim 8, wherein the second period of time is concurrent with the first period of time.

11. The method according to claim 1, wherein the gut microbiome modulating agent is administered at a dose of 10-20 mg/kg/day.

12. The method according to claim 1, wherein the cancer is breast cancer.

* * * * *